US012605046B2

(12) United States Patent
Matthison-Hansen

(10) Patent No.: US 12,605,046 B2
(45) Date of Patent: Apr. 21, 2026

(54) ELONGATE ARTICULATED BENDING SECTION BODY FOR AN INSERTION ENDOSCOPE

(71) Applicant: AMBU A/S, Ballerup (DK)

(72) Inventor: Kaspar Mat Matthison-Hansen, Helsingør (DK)

(73) Assignee: AMBU A/S, Ballerup (DK)

( * ) Notice: Subject to any disclaimer, the term of this patent is extended or adjusted under 35 U.S.C. 154(b) by 706 days.

(21) Appl. No.: 17/921,576

(22) PCT Filed: Apr. 22, 2021

(86) PCT No.: PCT/DK2021/050124
§ 371 (c)(1),
(2) Date: Oct. 26, 2022

(87) PCT Pub. No.: WO2021/219180
PCT Pub. Date: Nov. 4, 2021

(65) Prior Publication Data
US 2023/0165440 A1     Jun. 1, 2023

(30) Foreign Application Priority Data

Apr. 27, 2020     (DK) ............................ PA 2020 70265

(51) Int. Cl.
B29C 45/00          (2006.01)
A61B 1/00          (2006.01)
(Continued)

(52) U.S. Cl.
CPC .......... A61B 1/0011 (2013.01); A61B 1/0055 (2013.01); B29C 45/0017 (2013.01);
(Continued)

(58) Field of Classification Search
CPC ............ B29C 45/0017; B29C 45/0081; B29C 45/0046; B29C 45/2708;
(Continued)

(56) References Cited

U.S. PATENT DOCUMENTS 3,333,299 A * 8/1967 Florjancic ............ B22D 25/023
425/572
3,453,823 A * 7/1969 Mundt ................ B29C 45/0017
59/90
(Continued)

FOREIGN PATENT DOCUMENTS

EP          1994872 A1     11/2008
EP          3628208 A1     4/2020
(Continued)

OTHER PUBLICATIONS

Beal Glenn: "By Design: Polypropylene part design, Part 2—Living hinges", Jul. 25, 2002 (Jul. 25, 2002), pp. 1-4, XP055827042.
(Continued)

*Primary Examiner* — John J DeRusso
(74) *Attorney, Agent, or Firm* — Faegre Drinker Biddle & Reath LLP

(57)          ABSTRACT
A method for moulding an elongate articulated bending section body (4) for a medical device including a number of segments (7) interconnected via a number of hinge members (8). The method includes the use of a mould having a first number of sub-cavities where each of the sub-cavities has at least one external fluid inlet through which a liquified plastic material is injected into the mould. The sub-cavities are so distributed that each sub-cavity is separated from another sub-cavity by an odd number of sub-cavities without an external fluid inlet.

14 Claims, 3 Drawing Sheets

(51) Int. Cl.

| | |
|---|---|
| *A61B 1/005* | (2006.01) |
| *B29C 45/27* | (2006.01) |
| *B29C 45/33* | (2006.01) |
| *B29L 31/00* | (2006.01) |

(52) U.S. Cl.
CPC ...... *B29C 45/0046* (2013.01); *B29C 45/0081* (2013.01); *B29C 45/2708* (2013.01); *B29C 45/33* (2013.01); *B29C 2045/2709* (2013.01); *B29L 2031/7546* (2013.01)

(58) Field of Classification Search
CPC .... B29C 2045/2709; B29C 2045/2712; B29C 2045/2716; A61B 1/0011
See application file for complete search history.

(56) References Cited

U.S. PATENT DOCUMENTS

| | | | | |
|---|---|---|---|---|
| 4,095,932 | A | * | 6/1978 | Tome ................. B29C 45/0017 |
| | | | | 425/588 |
| 4,641,701 | A | * | 2/1987 | Yamamoto ............ B22D 17/24 |
| | | | | 164/90 |
| 5,325,845 | A | | 7/1994 | Adair |
| 9,820,634 | B2 | | 11/2017 | Simchony et al. |

| | | | |
|---|---|---|---|
| 2004/0199052 | A1 | 10/2004 | Banik et al. |
| 2011/0184232 | A1 | 7/2011 | Maxwell et al. |
| 2020/0100648 | A1 | 4/2020 | Jensen |
| 2020/0113415 | A1 | 4/2020 | Kristensen |

FOREIGN PATENT DOCUMENTS

| | | | |
|---|---|---|---|
| WO | 2019/002186 | A1 | 1/2019 |
| WO | 2019/175350 | A1 | 9/2019 |

OTHER PUBLICATIONS

International Preliminary Report on Patentability received for PCT Patent Application No. PCT/DK2021/050124, mailed on Nov. 10, 2022, 12 pages.
International Search Report and Written Opinion received for PCT Patent Application No. PCT/DK2021/050124, mailed on Aug. 2, 2021, 14 pages.
John et al., "Injection Molding: How to Mold Living Hinges With No Flexing Required", Aug. 24, 2016 (Aug. 24, 2016), pp. 1-3, XP055827038.
Peter et al., "Principles of Mold Design—General Remarks", Gastrow Injection Molds, Jun. 1, 2006 (Jun. 1, 2006), pp. 1-5, XP055825717.
First Technical Examination Report issued in Danish Patent Application No. PA 2020 70265, dated Sep. 28, 2020, 7 pages.

* cited by examiner

ELONGATE ARTICULATED BENDING SECTION BODY FOR AN INSERTION ENDOSCOPE

CROSS REFERENCE TO RELATED APPLICATIONS

This application is a National Stage entry under 35 U.S.C. § 371 of International Application No. PCT/DK2021/050124, filed Apr. 22, 2021, which claims priority from and the benefit of Danish Patent Application No. PA 2020 70265, filed Apr. 27, 2020; said applications are incorporated by reference herein in their entirety.

TECHNICAL FIELD

The present disclosure relates to a medical device, such as an endoscope, and in particular to the manufacture of an elongate articulated bending section body for such a medical device.

BACKGROUND

Insertion endoscopes typically comprises a handle at the proximal end gripped by an operator and a flexible elongate insertion tube terminated at the distal end in a tip part at the end of a highly bendable, e.g. articulated, bending section, controllable by the operator. The tip part normally comprises a visual inspection means such as a camera, and illumination means such as LED's or exit apertures of light fibres and whatever optics is needed in that connection. Electrical wiring for the camera and other electronics such as the LED lighting run along the inside of the elongate insertion tube from the handle to the tip at the distal end. When, as mentioned, the illumination is instead fibre-optic, the optical fibres run along inside of the elongate insertion tube.

Thus, the controllable bending section is normally an articulated section at the distal tip of the elongate insertion tube that can be controlled by the operator via control knobs arranged on the handle. Typically, this control is effected by tensioning or slacking pull-wires also running along the inside of the elongate insertion tube from the articulated tip part to a control mechanism of the handle. Furthermore, a working channel may run along the inside of the elongate insertion tube from the handle to the tip, e.g. allowing liquid to be removed from the body cavity or allowing the insertion of surgical instruments or the like into the body cavity.

Thus, using the controls allows the operator to advance the distal tip of the endoscope to a desired location by means of a series of actions involving inter alia bending the bending section in a desired direction, advancing the elongate insertion tube and turning the elongate insertion tube by turning the handle which is rigidly connected thereto. Negotiating a tortuous path of bends and turns to a location of interest may subject the elongate insertion tube including the distal controllable bending section to substantial forces including compression, torsion, and bending. The main body of the elongate insertion tube is essentially only bendable enough to follow the direction taken by the articulated bending section. In fact, it could be said that it is an essential part of the purpose of the elongate insertion tube to transmit the longitudinal pushing forces and rotary torsional forces from the handle to the distal end of the elongate insertion tube in order to allow these maneuvers.

In some types of endoscopes, such as colonoscopes, it is even known to provide a dual bending section, comprising a passive bending section proximal to an active bending section, i.e. between the highly flexible active bending section operated by steering wires and the less flexible main tube of a flexible endoscope. The passive bending section improves maneuverability in some clinical settings. In practice, the pull-wires form parts of Bowden cables, i.e. the pull-wires run freely inside tubes which, in turn, are fixed against longitudinal motion with respect to the handle and the insertion tube body.

In order to provide the bending section, it is known to provide an integrally moulded one-piece bending section body. Such an integrally moulded one-piece bending section body is normally an elongate cylindrical body, at least as seen in the overall perspective. In detail, the articulated bending section body has a number of segments with a space between them except for hinge members interconnecting neighboring segments. These segments typically include a proximal end segment for connection to the remainder of the insertion tube, a distal end segment accommodating optics, vision device, illumination and other electronics, and a number of intermediate segments arranged between the proximal segment and the distal segment. The segments generally comprise a number of passages for electrical cables and wires, pull-wires for the control, of the bending, and one or more large apertures accommodating tubes forming working and/or suction channels or the like.

Moulding such an integral bending section body in one-piece is somewhat difficult. Not only is it typically a small item, in bronchoscopes often with a diameter of only a few, e.g. 3, mm and a length between say 15 mm or 30 mm and with longitudinal passages, some of which only a few tenth of millimeters in diameter. The size, however, depends on the type, and endoscopes with somewhat larger bending sections also exist, e.g. colonoscopes where the outer diameter may be in the range of 8 mm to 12 mm and the length between 8 cm and 12 cm. In colonoscopes, however, the bending section is often more complex than in bronchoscopes. Moreover, because the individual segments are only interconnected through thin hinge members, such as foil hinges, multiple injection points for moulding material into the mould are necessary, because the material will not readily flow throughout the entire mould cavity. Because of the multiple injection points, and hence multiple flows into the mould cavity, there will be places where different flows meet and will have to fuse or melt together, in the following called welding zones. In such welding zones the mechanical strength of the material is likely to be reduced as compared to other part of the elongate articulated bending section body.

BRIEF DESCRIPTION OF THE DISCLOSURE

Based on this it is the object of the present invention to provide a method and a mould allowing the manufacture of an improved elongate articulated bending section for the use in medical devices, such as insertion endoscopes, and in medical systems incorporating such medical devices.

According to a first aspect of the disclosure this object is achieved in method for moulding an elongate articulated bending section body for a medical device, such as an insertion endoscope, said articulated bending section body comprising a number of segments including a proximal segment, a distal segment and a number of intermediate segments arranged between the proximal segment and the distal segment, where said segments are interconnected via a number of hinge members, said method comprising providing a mould having at least two separable mould parts forming a mould cavity corresponding essentially to the external shape of said elongate articulated bending section body, thereby providing a longitudinally extending row of sub-cavities corresponding to the number of segments, said sub-cavities being in fluid connection via passages corresponding to said number of hinge members, said mould having a first number of sub-cavities where each of said first number sub-cavities has at least one external fluid inlet in fluid communication with a source of liquified plastic material and through which a liquified plastic material is injected into the mould to form the articulated bending section body, wherein said first number of sub-cavities are so distributed along the longitudinal extending row of sub-cavities that each cavity in said number of sub-cavities is separated from another cavity in said number of sub-cavities by an odd number of sub-cavities without an external fluid inlet, injecting said liquified plastic material into said first number of sub-cavities via the external fluid inlets, and into the said odd number of sub-cavities via said first number of sub-cavities only, allowing the liquified plastic material to set to form said elongate articulated bending section body, and removing the elongate articulated bending section body from the mould.

According to a second aspect of the disclosure the object is achieved by a mould for moulding an elongate articulated bending section body for a medical device, such as an insertion endoscope, said articulated bending section body having a number of segments including a proximal end segment, a distal end segment and a number of intermediate segments arranged between the proximal segment and the distal segment, where said segments are interconnected via a number of hinge members, said mould comprising at least two separable mould parts forming a mould cavity corresponding essentially to the external shape of said elongate articulated bending section body, thereby providing a longitudinally extending row of sub-cavities corresponding to the number of segments, said sub-cavities being in fluid connection via passages corresponding to said number of hinge members, said mould having a first number of sub-cavities where each of said first number sub-cavities has at least one external fluid inlet adapted to be in fluid communication with a source of liquified plastic material and through which a liquified plastic material may be injected into the mould to form the articulated bending section body, wherein said first number of sub-cavities are so distributed along the longitudinal extending row of sub-cavities that each cavity in said number of sub-cavities is separated from another cavity in said number of sub-cavities by an odd number of sub-cavities without an external fluid inlet.

According to a third aspect of the disclosure, the object is achieved by an elongate articulated bending section body for a medical device, such as an insertion endoscope, manufactured using the method according to the first aspect of the disclosure or a mould according to the second aspect of the disclosure.

According to a fourth aspect of the disclosure, the object is achieved by a medical device, such as an insertion endoscope, comprising an elongate articulated bending section according to the third aspect of the disclosure.

According to a fifth aspect of the disclosure, the object is achieved a system comprising a medical device according to the fourth aspect of the disclosure and a display unit connectable to said medical device.

Thereby an improved elongate bending section body free of welding zones in critical areas can be achieved. In particular, the welding zones can be designed to lie in areas where there is the largest bulk of material and/or where mechanical stresses will be least during use. In particular, welding zones at or near the hinge members can be avoided.

According to a preferred embodiment of the first aspect of the invention, said odd number of sub-cavities without an external fluid inlet is one. This provides a short flow distance and ensures that the welding zone occurs within the body of a segment, rather than at a hinge.

According to some preferred embodiments, the sub-cavities are generally symmetrical about a longitudinal centre plane, and as seen along the longitudinal direction said external fluid inlets are arranged with off-sets in alternating directions from said longitudinal centre plane. This further aids in controlling the in-flow of injected moulding material and the location of the welding zone.

BRIEF DESCRIPTION OF THE FIGURES

The disclosure will now be made in greater detail based on non-limiting exemplary embodiments and the appended drawings, on which.

DETAILED DESCRIPTION

Figures 1, 2:
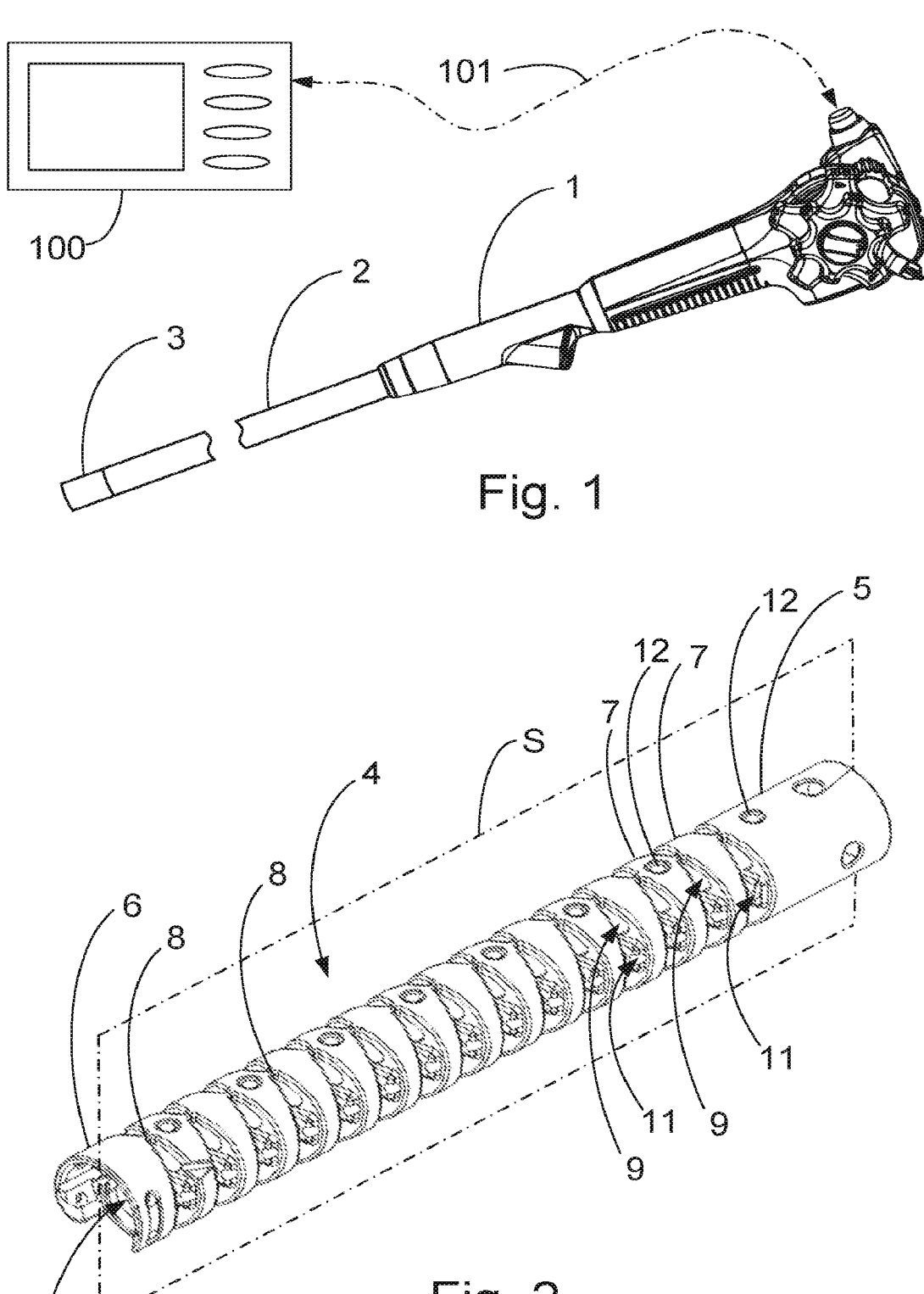
FIG. 1 shows a medical system comprising a display unit and an endoscope with an elongate articulated bending section body according to the disclosure.
FIG. 2 shows a first embodiment of an elongate articulated bending section body according to the disclosure.

Turning first to FIG. 1 an overall medical system is shown. The medical system comprises a medical device exemplified by an endoscope 1 and a display unit 100 to which the endoscope 1 is connected by means of cable or a wireless connection 101. At the distal end of the insertion endoscope 1 the insertion tube 2 is terminated in a bending section 3. The bending section 3 comprises an elongate articulated bending section body 4 shown in various embodiments in FIGS. 2 to 4, but not visible in FIG. 1 as it is covered by an external sheath.

Figures 3, 4:
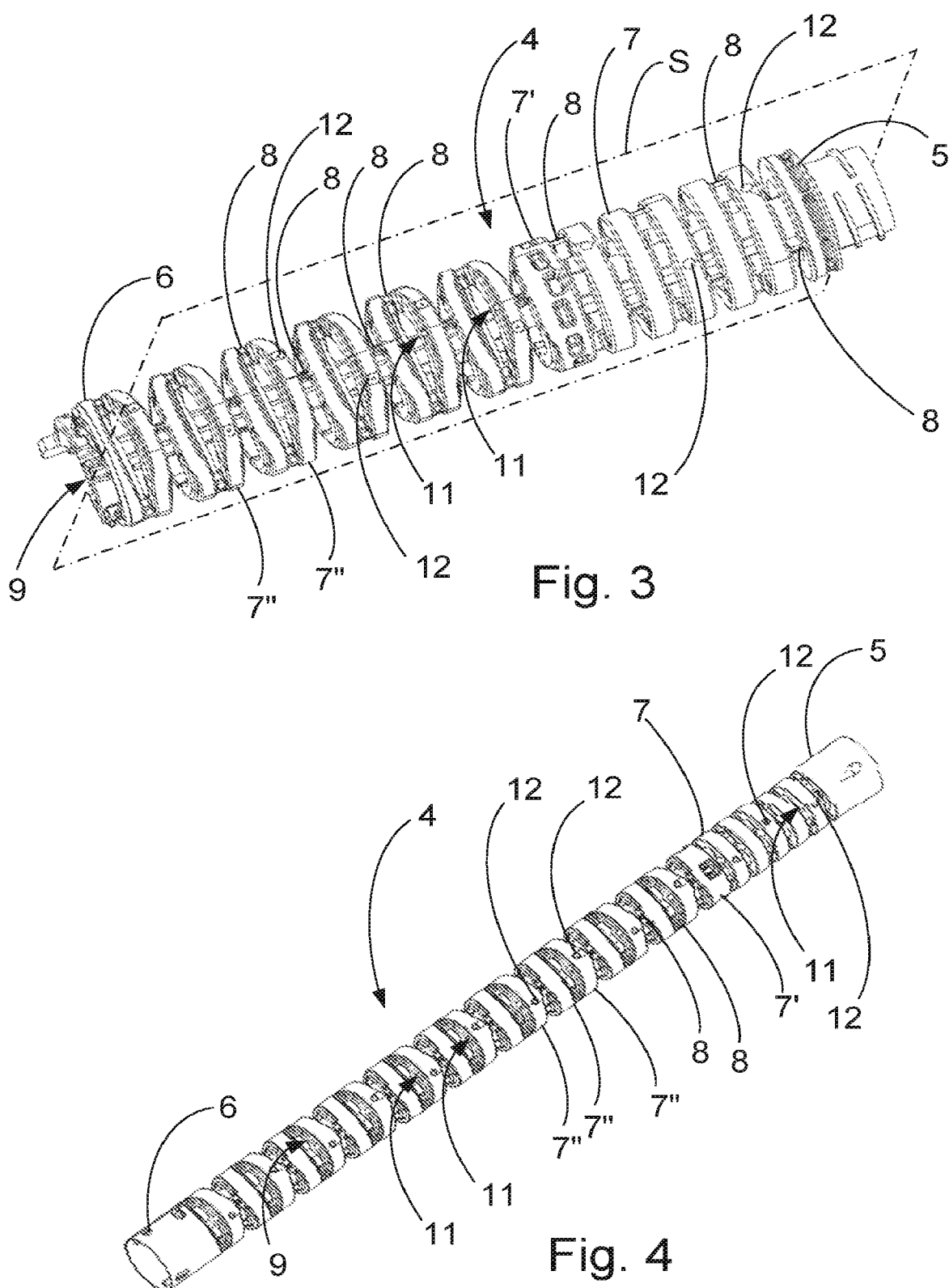
FIG. 3 shows a second embodiment of an elongate articulated bending section body according to the disclosure.
FIG. 4 shows a third embodiment of an elongate articulated bending section body according to the disclosure, and FIG. 5 schematically shows a mould for manufacturing an elongate articulated bending section body according to the disclosure.

Various embodiments of the bending section body 4 are shown in FIGS. 2 to 4. The bending section bodies 4 are shown in their relaxed, as made, state, that is to say without any external forces acting on them, and reference in the following are made to them in that state. Throughout the drawings the same reference numerals are used for identical or corresponding features.

Figure 5:
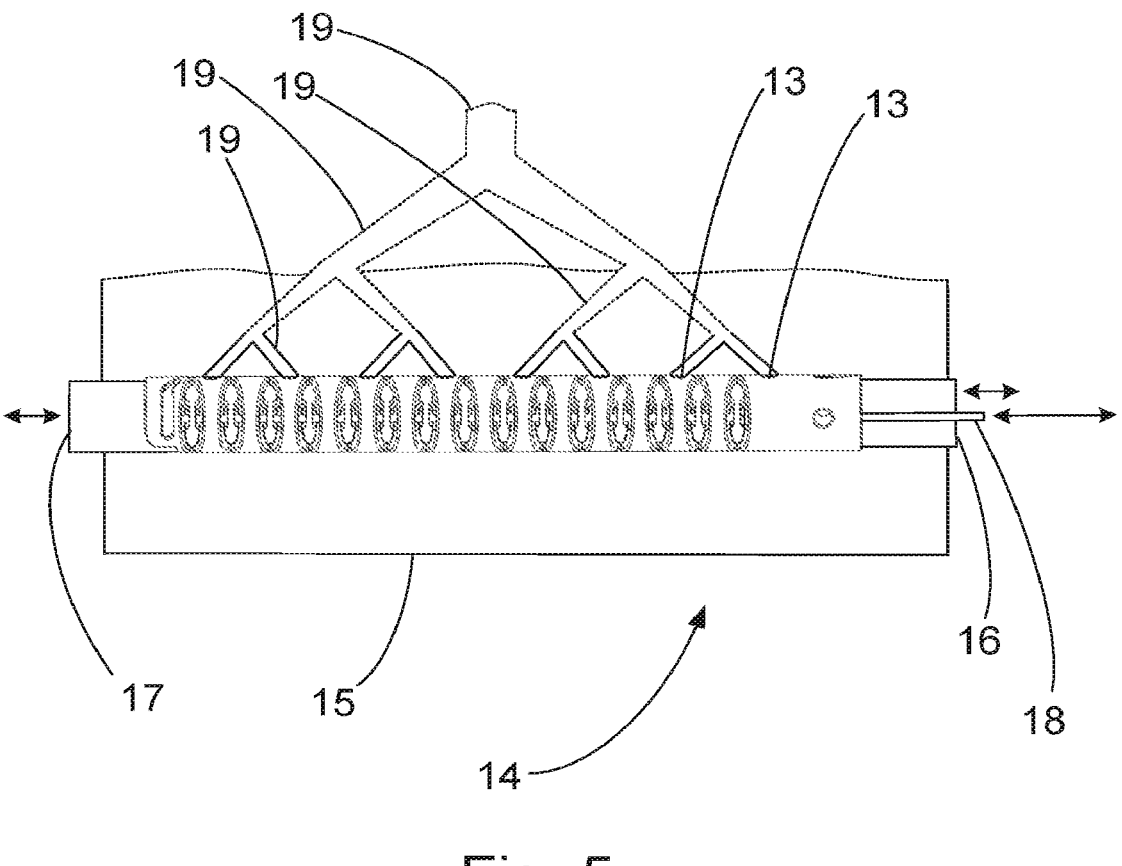

In FIG. 2 the bending section body 4 comprises a proximal segment 5 adapted for connection to the insertion tube 2, a distal segment 6 adapted for accommodating optics, vision device, illumination and other electronics in a manner per se known and not illustrated. Between the proximal segment 5 and the distal segment 6 a number of intermediate segments 7 are arranged. In FIG. 2 there are fourteen intermediate segments, so that the entire row of segments totals sixteen but the number of intermediate segments 7 could both be higher or lower depending on the actual design and purpose of the medical device. Between the segments a number of integrally moulded hinge members 8 are arranged, such as in particular integrally moulded foil hinges. The hinge members 8 in the embodiment of FIG. 2 are all arranged in the same longitudinal centre plane S essentially defining a symmetry plane about which the elongate articulated bending section body 4 is symmetrical or largely symmetrical, at least as far as the external features are concerned. Internally, the elongate articulated bending section body may comprise apertures, such as passages 9 for electrical wiring, optical fibres or the like, passages 10 for a working or suction channels, and passages 11 for pull-wires effecting the articulation of the bending section. Some of these passages could deviate from the symmetry as this is not important for the present disclosure. As shown, every second segment comprises a mark 12 corresponding to an external fluid inlet 13 of the injection mould 14 in which the elongate articulated bending section body 4 has been moulded, cf. FIG. 5. Material corresponding to the external fluid inlets 13 as such has been broken away after manufacture. In FIG. 2 the mould comprises two halves separable in opposite directions from the symmetry plane S and with the external fluid inlets 13 in the symmetry plane S. In FIG. 5 one mould half 15 is shown, together with various retractable cores 16, 17, 18. When closed, the mould 14 thus comprises a number of sub-cavities, each corresponding to a segment of the resulting elongate articulated bending section 4, each sub-cavity being separated from its neighbor except for the passages adapted for forming the hinge members 8, which thus serve as internal fluid inlets for those sub-cavities. As mentioned, the mould 14 comprises a number of retractable and/or collapsible cores 16, 17, 18 for forming the internal passages 9, 10 11. As will be understood every second of the sub-cavities does not comprise an external fluid inlet and may be referred to as an "inlet-free sub-cavity" while the sub-cavities including external fluid inlets may be referred to as "fluid-inlet sub-cavities". During injection of the liquified moulding material into the mould via suitably configured feed channels 19, the inlet-free sub-cavities sub-cavities will be filled only indirectly with moulding material, i.e. via the sub-cavities with the external fluid inlets 13 and through the passages adapted to form the hinge members 8. With identical or largely identical sub-cavities and due consideration of the deviations of the sub-cavities for the proximal end segment 5 and the distal end segment 6, an odd number of cavities, in casu one, between each sub-cavity with an external fluid inlet, the flows of liquified moulding material from two sub-cavities with an external fluid inlet 13 can be made to meet and fuse together in the middle of intermediate sub-cavity without an external fluid inlet 13. The welding zone thus occurs in the bulk of the material of the intermediate segment 7 as far away from the more critical hinge members 8 as possible.

Thus, when the liquified moulding material, which is preferably a plastic material, has been allowed to set to form said elongate articulated bending section body 4, the elongate articulated bending section body 4 can safely be removed from the mould 14 without the risk of breaking at the hinge members 8 at this stage or later during use.

Turning now to FIGS. 3 and 4, slightly more complex articulated bending section bodies 4, where hinge members 8 lie in two planes, are shown. Thus, bending sections 2 incorporating these may bend in four directions, i.e. up, down, left and right, whereas with the elongate articulated bending section body 4 of FIG. 2 bending is only possible in one plane e.g. up and down (or left and right depending on how you see it). As shown, the segments 7 are shaped differently than a transition segment 7' and the segments 7" on the opposite side of the transition segment 7'. The transition segment 7' is one of the intermediate segments and comprises a plurality of passages along its periphery. External fluid inlets 13 supply material to the segments on both sides of the transition segment 7'.

As will be noted, the marks 12 corresponding to the external fluid inlets do not lie in the same symmetry plane, but rather are alternatingly arranged on either side of the symmetry plane S. This further improves the control over the location of the welding zones in the segments 5, 6, 7 moulded in sub-cavities not provided with an external fluid inlet. In particular it ensures that the welding zones are away from the hinge members 8 on either side of an intermediate segment 7 which are off-set with an angle of 90 degrees with respect to each other.

Although the symmetry plane is not shown in FIG. 4 it will be evident that also in that embodiment the external fluid inlets of the sub-cavities corresponding to every second intermediate segment are of the mould and, hence, the resulting marks 12 are arranged on either side of such a symmetry plane.

As will be understood, the mould (not shown) for the embodiments of the elongate articulated bending section body of FIGS. 3 and 4 will comprise four mould quarters, retractable in orthogonal directions to allow for the easy manufacture of the 90 degree off-set hinge members 8, as well as retractable and/or collapsible cores for the longitudinal passages.

The skilled person will understand that numerous embodiments of the elongate articulated bending section body are possible, and that features described above in conjunction with one embodiment is freely interchangeable with the other disclosed embodiments, as well as incorporable in embodiments not shown. The skilled person will also understand that deviation from the preferred odd number of one sub-cavity between sub-cavities with an external fluid inlet such as three or five will be possible.

What is claimed is:

1. A method for molding a bending section body for a medical device, the method comprising:
    injecting a liquified plastic material through fluid inlets of a mold to form segments and hinges of the bending section body, the hinges formed in passages of the mold, and the segments formed in sub-cavities of the mold, the segments being interconnected by the hinges,
    wherein the sub-cavities are positioned parallel to each other and along a length of the mold and comprise fluid-inlet sub-cavities and inlet-free sub-cavities, each of the fluid-inlet sub-cavities being separated from another of the fluid-inlet sub-cavities by one of the inlet-free sub-cavities,
    wherein said injecting comprises injecting the liquified plastic material into the fluid-inlet sub-cavities solely through the fluid inlets and into the inlet-free sub-cavities through the passages,
    wherein a longitudinal center plane traverses the sub-cavities, and
    wherein the fluid inlets are offset in alternating directions from the longitudinal center plane.

2. The method of claim 1, wherein the sub-cavities are symmetrical about the longitudinal center plane.

3. The method of claim 1, wherein the mold comprises at least two mold parts, the method further comprising separating the at least two mold parts to remove the bending section body in one piece.

4. The method of claim 3, wherein the at least two separable mold parts are separable along the longitudinal center plane.

5. The method of claim 1, wherein the passages interconnecting the sub-cavities are offset 90 degrees from any adjacent passages.

6. The method of claim 1, wherein the sub-cavities comprise a first set of the sub-cavities, a second set of the sub-cavities, and a transition sub-cavity positioned between the first set and the second set, the sub-cavities in the second set being different from the sub-cavities in the first set and being different from the transition sub-cavity.

7. The method of claim 6, wherein the transition sub-cavity is configured to impart peripheral passages onto the segment molded therein.

8. The method of claim 7, wherein the sub-cavities in the first set and in the second set are devoid of peripheral passages.

9. The method of claim 6, wherein the transition sub-cavity is configured to impart peripheral passages onto the segment molded therein, and wherein the transition sub-cavity is one of the inlet-free sub-cavities.

10. The method of claim 1, wherein said injecting comprises injecting the liquified plastic material into the fluid-inlet sub-cavities until the liquified plastic material flows out of the fluid-inlet sub-cavities through the passages and into the inlet-free sub-cavities, wherein the liquified plastic material flows from a pair of the fluid-inlet sub-cavities into one of the inlet-free sub-cavities positioned between the pair until the liquified plastic material flowing from the pair of the fluid-inlet sub-cavities fuses in a welding zone, and wherein the welding zone is spaced from the hinges connecting the pair of the fluid-inlet sub-cavities to the one of the inlet-free sub-cavities.

11. The method of claim 10, wherein the sub-cavities comprise a first set of the sub-cavities, a second set of the sub-cavities, and a transition sub-cavity positioned between the first set and the second set, the sub-cavities in the second set being different from the sub-cavities in the first set and being different from the transition sub-cavity.

12. The method of claim 11, wherein the transition sub-cavity is configured to impart peripheral passages onto the segment molded therein.

13. The method of claim 12, wherein the sub-cavities in the first set and in the second set are devoid of peripheral passages.

14. The method of claim 11, wherein the transition sub-cavity is configured to impart peripheral passages onto the segment molded therein, and wherein the transition sub-cavity is one of the inlet-free sub-cavities.

* * * * *